US00PP09348P

United States Patent [19]

Bridgen

[11] Patent Number: Plant 9,348

[45] Date of Patent: Oct. 31, 1995

[54] ALSTROEMERIA 'PATRIOT'

[75] Inventor: Mark P. Bridgen, Storrs, Conn.

[73] Assignee: University of Connecticut, Storrs, Conn.

[21] Appl. No.: 355,062

[22] Filed: Dec. 13, 1994

[51] Int. Cl.[6] ..... A01H 5/00

[52] U.S. Cl. ..... Plt./87.1

[58] Field of Search ..... Plt./87.1

*Primary Examiner*—James R. Feyrer

*Attorney, Agent, or Firm*—Hamilton, Brook, Smith & Reynolds

[57] ABSTRACT

A new and distinct cultivar of Alstroemeria named 'Patriot' is characterized by large purple blossoms which have numerous longitudinal dark purple streaks on its inner circle of tepals; the top two tepals of this inner group of three also have white on their lower portions. The individual florets are produced in large numbers on short peduncles. The plant is also distinguished by its short (approximately 32 cm. when grown in full sun), but strong, stems and its upright and vigorous growth habit. There is a continuous production of flowers on its umbel arrangement of branches during each of its blooming seasons.

1 Drawing Sheet

SUMMARY OF THE INVENTION

This new and distinct cultivar of the botanical genus Alstroemeria (Lily-of-the-Incas, Inca Lily, or Peruvian Lily) is a product of my breeding program at the University of Connecticut in Storrs, Conn. The primary objective of my breeding program was the creation of new Alstroemeria cultivars for pot production and garden cultivation. This Alstroemeria plant originated as a seedling number A128 and was selected from a group of unnamed and unpatented plants that were gamma-irradiated as seeds.

This plant was selected for propagation and is distinguishable from all other Alstroemeria varieties because it combines a distinctive purple flower coloration with a short growth habit and strong, upright flower stems. Numerous florets are produced on each flower stem. Asexual propagation of this new plant by root division was carried on under my direction at the University of Connecticut; successive generations of this plant have demonstrated that the distinctive characteristics of the parent hybrid hold true from generation to generation and appear to be firmly fixed. Micropropagation and traditional asexual propagation by rhizome division of this new cultivar is now being carried on at the University of Connecticut.

This cultivar has been observed in the greenhouse and in the field for several years but has not been observed under all possible environmental conditions. The phenotype may vary with variations in environment such as light intensity, temperature, nutrition and daylength.

BRIEF DESCRIPTION OF THE DRAWING

This new cultivar of Alstroemeria plant is illustrated by the accompanying photographic drawings in full color showing an umbel of the plant with buds and flowers in different stages of opening. The color renditions are believed to be as close to the specified colors as is possible to obtain by conventional photographic procedures.

DETAILED DESCRIPTION OF THE NEW VARIETY

The following is a detailed description of my new Alstroemeria plant with color designations according to the R.H.S. Colour Chart of The Royal Horticultural Society of London, England. Colors were confirmed with CIELAB coordinates that were measured with a Minolta CR-200b Color Meter (Minolta, Ramsey, N.J.). The following observations, measurements, and comparisons describe plants grown in Storrs, Conn. under field conditions in full sun.

The Plant

Origin: Seedling.

Parentage: This plant resulted as a selection from a group of plants that were gamma irradiated as seeds.

Classification:

- *Botanic.*—Alstroemeria hybrid L.
- *Commercial.*—Alstroemeria; Lily-of-the-Incas; Inca Lily; Peruvian Lily.

Form: Herbaceous plant arising from an underground rhizome and having short, stout flowering stalks with flower-bearing branches of simple umbel form at its top.

Height: Approximately 32 cm.

Growth: Strong and upright.

Root stock: Tuberous.

Foliage:

- *Quantity.*—Many.
- *Number of leaves.*—Average of 38 per vegetative stem. Average of 24 per inflorescence.
- *Size of leaf.*—Length: 9.2 cm. Diameter at widest point: 2.8 cm.
- *Leaf shape.*—Simple, linear, resupinate leaves with parallel venation that are arranged alternately; the shape of the leaves is elliptic with extended bases and broadly acuminate apices; leaf margins are entire.
- *Texture.*—Glabrous leaf surfaces.
- *Color.*—Dark green on both upper and under sides.

Rhizomes:

- *Color.*—White.

The Bud

Form: Pear shaped becoming long and more pointed just before opening.

Size:

- *Diameter.*—Approximately 1 cm. as the bud begins to form external pigments.
- *Length.*—Approximately 1 cm. as the bud begins to form external pigments.

Calyx: This plant's flower bud has no separate calyx and corolla; the six tepals of the flower are a perianth and divide simultaneously.

Opening rate: Normal.

Peduncle:
*Length.*—Approximately 4.5 cm. to primary floret.
*Color.*—Green turning dark purple as it reaches anthesis.

The Flower

Blooming habit: Continuous and profuse after flower initiation.
Flower size: Large.
*Diameter.*—4.8–5.3 cm.
*Depth.*—5.3 cm.
Number of florets/inflorescence: Average 10.
Borne: Singly.
Shape: Flowers are zygomorphic, protandrous, and epigynous with inferior ovaries; flowers arise in a terminal bracted umbel of cymes. Mature blooms are funnel-shaped with tepal tips curling outward.
Inflorescence length: 32–41 cm.
Petalage:
*Number of petals.*—Six tepals.
*Arrangement.*—Two concentric circles of three tepals each.
*Form.*—The 3 outer tepals are spatulate with emarginate to mucronate apices that pinch together. The extreme 1–2 mm tip is greenish. The 3 inner tepals are also spatulate but are more narrow than the 3 outer tepals and have apiculate apices.
*Texture.*—Leathery.
*Appearance.*—Shiny.
*Color of petals.*—Outer tepals — The purple color is primaryly 72B-C, but it does get more purple 72A toward the apex and have lighter gradations toward the base. The extreme apex is light green 138B. Inner tepals — The bottom tepal of this central ring of 3 is the same color as the outer tepals, except there are numerous, well-defined longitudinal dark purple 79A streaks throughout. The two upper tepals of this central ring of 3 are white 155D on their lower portions and purple 72B-C on their top portions; these upper tepals have similar well-defined longitudinal dark purple 79A streaks throughout.
Peduncle:
*Length.*—4.5 cm.
*Color.*—Light green.
Persistence: The tepals fall off at a senescence.
Lasting quality:
*On plant.*—Approximately 20–28 days.
*As a cut flower.*—Approximately 10–14 days.
Main stem or stalk:
*Length.*—32–41 cm.
*Character.*—Strong and upright.
*Number of leaves.*—Average of 24 per inflorescence.
*Size of leaf.*—Length: 10.2 cm. Diameter at widest point: 2.9 cm Reproductive Organs Stamens:
*Number.*—Six.
*Arrangement.*—One opposite each petal.
Anthers:
*Size.*—6–9 mm.
*Color.*—Light brown.
Filaments:
*Size.*—25–40 mm.
*Color.*—Pinkish purple.
Pistils:
*Number.*—One.
*Color.*—Pale purple.
Stigma:
*Color.*—Pale purple.

Fruit

Fertility: Fertile tetraploid (2n=4x=32).
Shape: Capsular.
Color at maturity: Purplish/dark red.

This cultivar of Alstroemeria is characterized by the distinctive coloration and short peduncles of its flowers which do not closely resemble that of any other Alstroemeria plant previously known to me as well as its short growth habit. My new variety of Alstroemeria most nearly resembles "Stalmon" (U.S. Plant Pat. No. 6,034) but differs in height of the plant. "Stalmon" is very tall; whereas, "Patriot" is short. The large blossoms of this cultivar are purple with numerous longitudinal dark purple streaks on its inner circle of tepals; the top two tepals of this inner group of three also have white on their lower portions. The individual florets are produced in large numbers on short peduncles. The plant is also distinguished by its short (approximately 32 cm. when grown in full sun), but strong, stems and its upright and vigorous growth habit. There is a continuous production of long-lasting flowers on its umbel arrangement of branches during each of its blooming seasons.

I claim:

1. A new and distinctive Alstroemeria plant substantially as herein shown and described, distinguished by its unique flower color, short growth habit, strong and numerous flowering stems, and numerous florets per inflorescence.

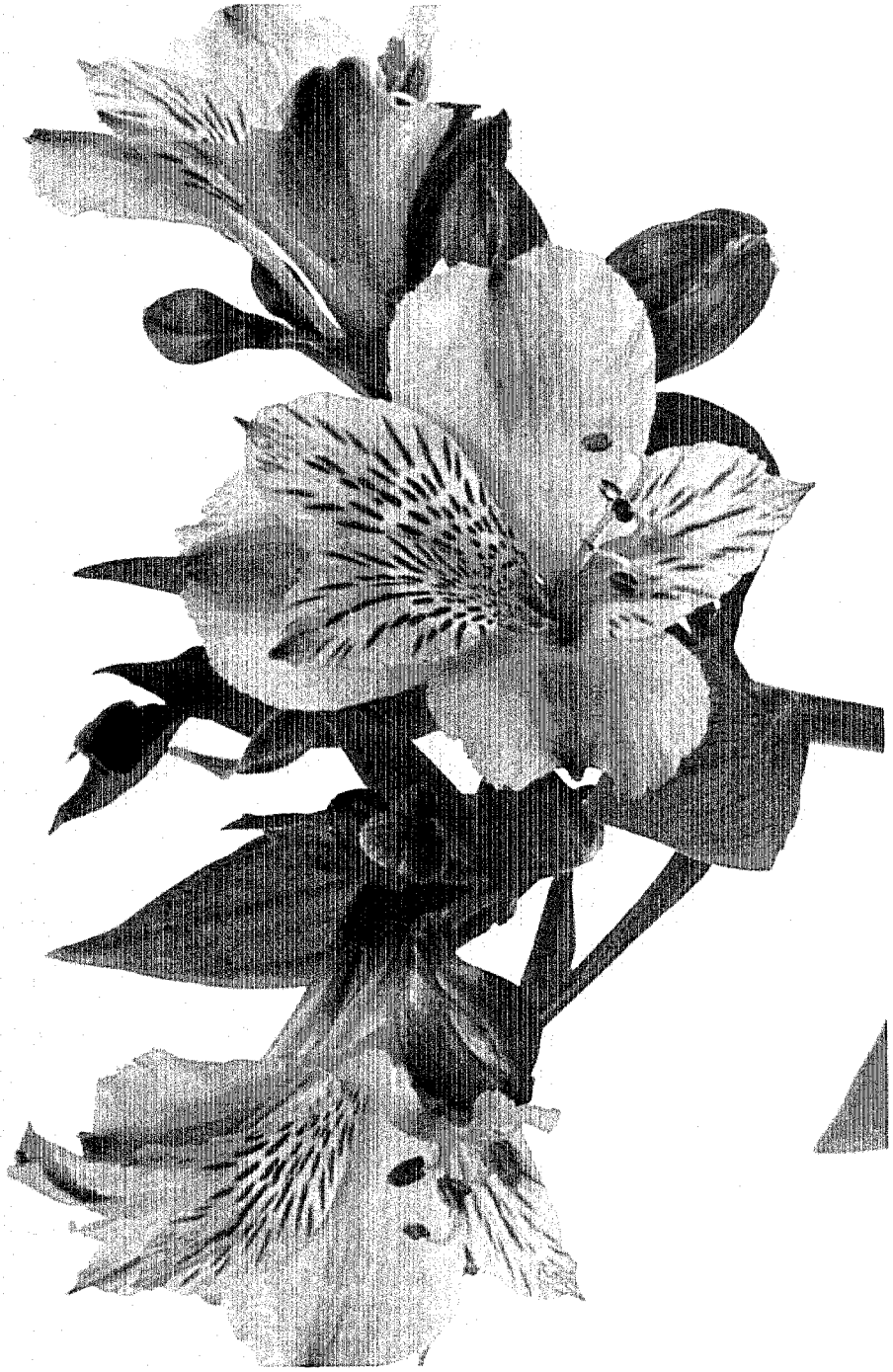

* * * * *